United States Patent [19]
Lee

[11] Patent Number: 5,722,420
[45] Date of Patent: Mar. 3, 1998

[54] EMG BIOFEEDBACK TRACTION MODALITY FOR REHABILITATION

[75] Inventor: Ming-Yih Lee, Taoyuan, Taiwan

[73] Assignee: National Science Council, Taiwan

[21] Appl. No.: 562,222

[22] Filed: Nov. 28, 1995

[51] Int. Cl.[6] ............................................. A61B 5/04
[52] U.S. Cl. .............................. 128/733; 601/23; 482/4
[58] Field of Search .................... 128/733; 601/23; 482/4–6

[56] References Cited

U.S. PATENT DOCUMENTS

| | | | |
|---|---|---|---|
| 5,054,774 | 10/1991 | Belsito | 272/130 |
| 5,277,197 | 1/1994 | Church et al. | 128/733 |
| 5,403,251 | 4/1995 | Belsito et al. | 482/4 |
| 5,474,083 | 12/1995 | Church et al. | 128/733 |
| 5,484,355 | 1/1996 | King, II et al. | 601/73 X |
| 5,484,389 | 1/1996 | Stark et al. | 601/34 |
| 5,512,025 | 4/1996 | Dalebout et al. | 601/23 X |
| 5,540,235 | 7/1996 | Wilson | 128/733 X |
| 5,597,373 | 1/1997 | Bond et al. | 482/4 |

*Primary Examiner*—Francis Jaworski
*Attorney, Agent, or Firm*—Jeing & Chang

[57] ABSTRACT

A new design of therapeutic traction modality with closed loop traction force control based on EMG signals from selected muscle is developed for rehabilitation. This modality includes main traction controller, a high signal-to-noise ratio EMG scanning and processing units, A/D and D/A computer interface hardware, on-line self-adjusted traction force actuating unit, biofeedback control software, and audio/visual alarms. This new traction modality provide a breakthrough milestone for the open loop control architecture of conventional motorized traction machine. The kernel of this invented modality is to adaptively adjusting traction force based on real time detected EMG signals to ensure the safety, comfort, and effectiveness of traction therapy.

15 Claims, 9 Drawing Sheets

EMG BIOFEEDBACK TRACTION MODALITY FOR REHABILITATION

FIELD OF THE INVENTION

This invention relates to a new design of cervical traction therapeutic modality. In particular, this invention relates to a cervical traction therapeutic modality with close loop traction weight control based on an EMG biofeedback.

BACKGROUND OF THE INVENTION

Neuro-muscular deterioration has been a common problem not only for elderly people but also for younger people who had received improper therapy for work, recreation, sport or automobile related injuries. The costs confronting to those with neuro-muscular disabilities include costs for medical care, maintenance, attendance care, nursing home and home care and lost wages for the disabled and their family members. To prevent such losses for neuro-muscular patients, a comprehensive therapeutic program is required.. However, the effectiveness of a therapeutic program relies not only on the skills of medical physicians, but also on the availability of appropriate medical equipment. Therefore, how to increase the efficiency and effectiveness of clinical/therapeutic devices remains an important and challenging issue.

Today, an average person will probably spend more time in sitting and standing than in resting due to the busy workloads and pressures in one's daily life. As a result, our bodies rely heavily on our spinal cords for weight supports in most of the day. In addition, many people become victims of undesirable neck and back pains due to incorrect postures and excessive sporting. Clinically, the intervertebral disc herniation and spondylosis are the common causes of the compression of spinal nerves. The nonsteroid anti-inflammatory or muscle relaxant drugs are usually prescribed by physicians to relief pain for patients with such spinal nerve compression problems. However, these medications may cause stomach upset and are not always effective in some of the patients. In these conditions, the cervical and pelvic traction are the common physical therapy methods in addition to electrotherapy [Valtemen et al.. *Scand J Rehabil Med;* 2, 1: 29–36, 1970; Nanno, *Nippon IKa Duigaku Zusshi;* 61,2:137–147, 1994, LaBan et al., *Arch Phys Med Rehabil;* 113, 3:245–246, 1975; Wong et al., *Spine;* 17,2:136–138, 1992; *Jackson,* Charles C. Thomas Publisher, 1978; Delacerda, *J Orthopaedic and Sport Physical Therapy,* 1: 205–209, 1980].

Commercial therapeutic traction modality are available in many different models. However, the main functions of these models include mostly manual adjustment of traction force and timing control of traction pull/hold phases. The drawbacks for these models are: (1) the traction pull/hold phase control is based on an open loop control structure which may cause muscle injury, neck soreness or pain after traction due to improper traction angle, muscle spasm during traction therapy; (2) the adjustment of traction force is based only on the subjective judgment and personnel experience of the attending therapists; (3) no subjective and quantitative measures for assessing the adequacy of traction force; and (4) no correction between muscle relaxation and traction therapeutic protocols.

From literature review, most researches on EMG signal focused on EMG visual biofeedback, EMG diagnostic measures, EMG muscle activity analysis, EMG function stimulation, and EMG muscle relaxation assessment [Jette et al., *Physical Therapy;* 65, 8:1173–1176, 1985; Sundeline et al., *Ergonomic;* 32, 5: 527–537, 1989; Sihvonen et al., *Arch Phys Med Rehabil;* 1080–1087, 1991; Marinacci et al., *Bulletin of Los Angels Neurological Society,* 25;57–71, 1961; basmajian J. V. *Science;* 141;440–441; Brundy J., *Biofeedback in chronic neurological cases: therapeutic electromyography.,* In L. White & B. Tursky (eds). *Clinical Biofeedback. Efficiency and Mechanism,* New York. Guilford Press, 1992; and Binder-Macleod, S. A., *Biofeedback in stroke rehabilitation.,* In J. V. Basmanjian (ed), *Biofeedback: Principles and Practice for Clinicians* (2th ed), Baltimore, Williams & wilkins, 1983]. Researcher claimed that the muscle relaxation is a determining factor on the effectiveness of traction therapy. Also, the direct relationship between muscle activity and muscle relaxation has been well documented in the literature. Therefore, the use of EMG signals to evaluate muscle relaxation is the commonly accepted method. However, the implementation of EMG biofeedback in cervical traction adaptive control has never been reported. Apparently, there is a need, among others, for a traction machine capable of integrating EMG biofeedback functions to provide traction force and time control to achieve best therapeutic effects.

SUMMARY OF THE INVENTION

It is therefore an objective of the invention to provide for a new design of cervical traction modality with closed loop traction force control based on EMG signals from paraspinal muscle to adaptively adjust traction force based on on-line detected EMG signals to ensure the safety, comfort, and effectiveness of traction therapy.

It is another objective of the invention to provide for a traction machine capable of integrating the EMG signal biofeedback system, closed loop traction force control software and the audio-visual system as one single operable unit to perform the functions of diagnostic measures, muscle activity monitoring, EMG biofeedback, muscle relaxation assessment and traction therapy.

It is a further objective of the invention to provide for a central control system capable of integrating multiple traction machines, EMG signal biofeedback system, audio-visual system and the computer interface for the hardware and software necessary to achieve a centrally controlled therapeutic traction system.

The present invention provides for an adaptive traction modality with closed loop traction force control based on EMG biofeedback signals recorded from a patient's neuro-muscular lesion for relieving neck pain and cervical radiculopathy in rehabilitation. The traction modality comprises a main controller for the control of traction force and a single channel high signal-to-noise ratio EMG scanner and signal processing units for receiving and processing EMG signals recorded from the neuro-muscular lesion of the patient. The main controller and the EMG scanner is connected through a main controller/EMG scanner interface to provide a communication means between the main controller and the EMG scanner and processing units for closed loop traction force monitor and adjustment. The main controller is also connected to a traction actuator through a traction force control interface to provide a communication means between the main controller and the traction modality for traction force control. In addition, the traction modality further comprises a traction control window graphical display interface to display EMG signal data and to make on-line in-process adjustment for traction force and remaining traction time.

The basic operation of traction modality includes entering the patient's background information through the graphical display interface to the main controller to calculate a upper and lower EMG control limits as a safety precaution. The actual EMG biofeedback signals received from the patient's neuro-muscular lesion are compared with the control limits to determine an optimal traction. When the actual EMG biofeedback signals exceed the upper and lower EMG control limits, an automatic warning system is activated to warn the therapist and to adjust the traction force automatically to provide a safe, comfort therapy. The traction modality is also equipped with a multimedia audiovisual system to effectuate a biofeedback traction therapy.

BRIEF DESCRIPTION OF THE DRAWINGS

A more complete understanding of the invention and its advantages will be apparent from the Detailed Description of the Preferred Embodiment taken in conjunction with the accompanying drawings in which.

DETAILED DESCRIPTION OF THE INVENTION

Figure 4:
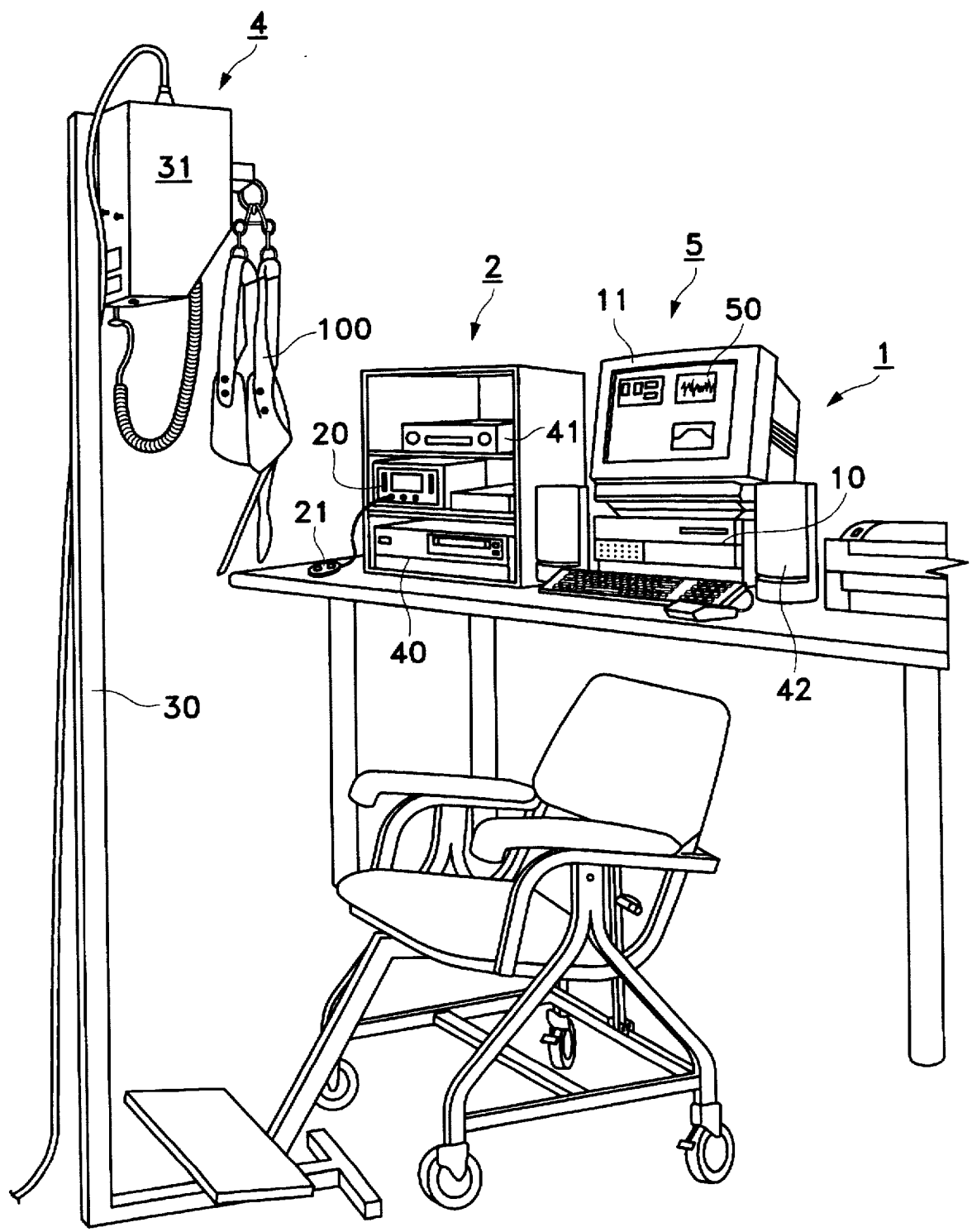
FIG. 4 shows a slant view of the whole picture of the EMG biofeedback controlled traction modality of the present invention.
Figure 5:
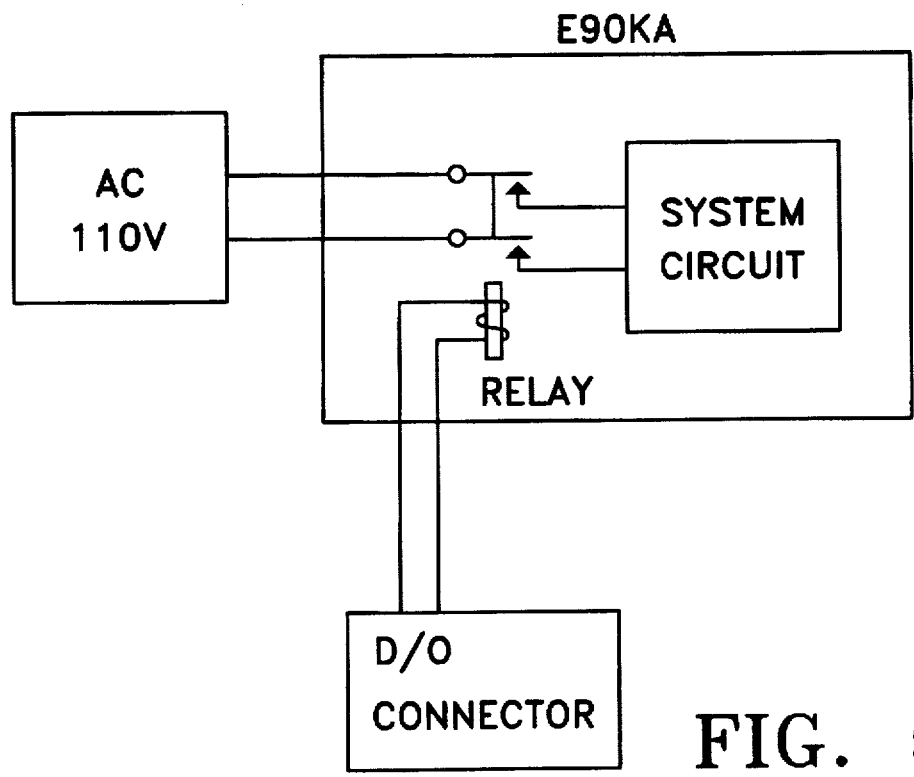
FIG. 5 illustrates a flow diagram for the programmable power on/off switch of the traction modality.
Figure 6:
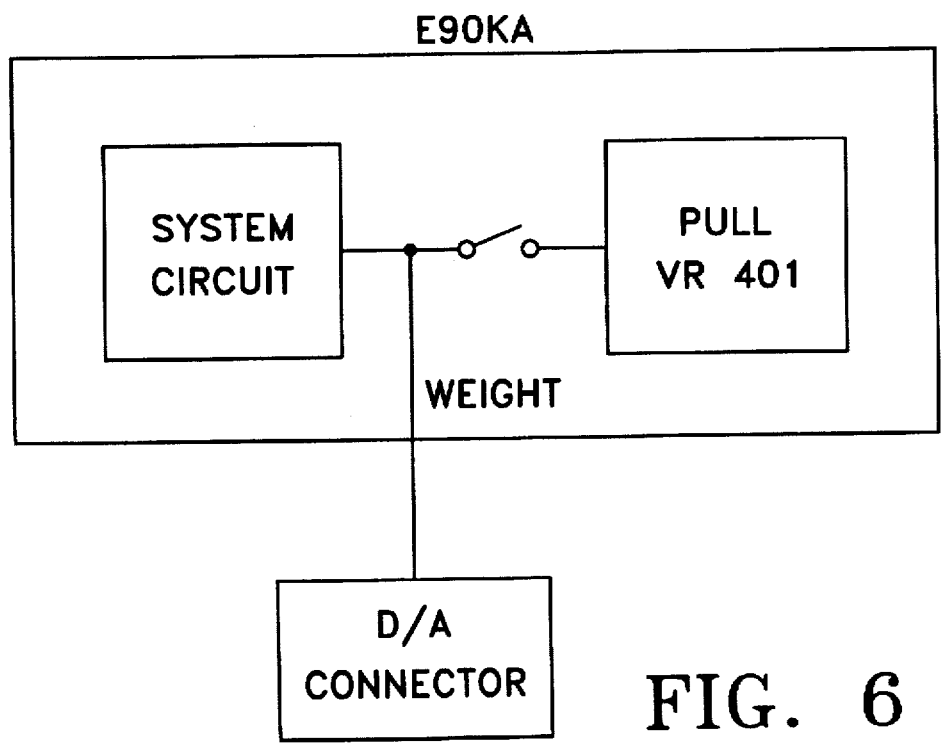
FIG. 6 illustrates a flow diagram for the programmable traction force control switch.
Figure 7:
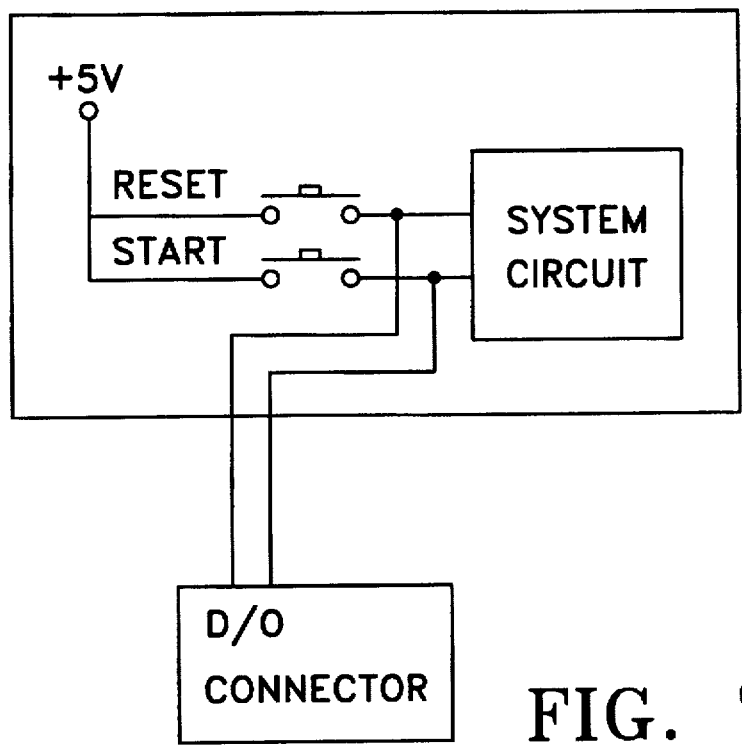
FIG. 7 illustrates a flow diagram for the programmable traction start/shop control switch.
Figure 8:
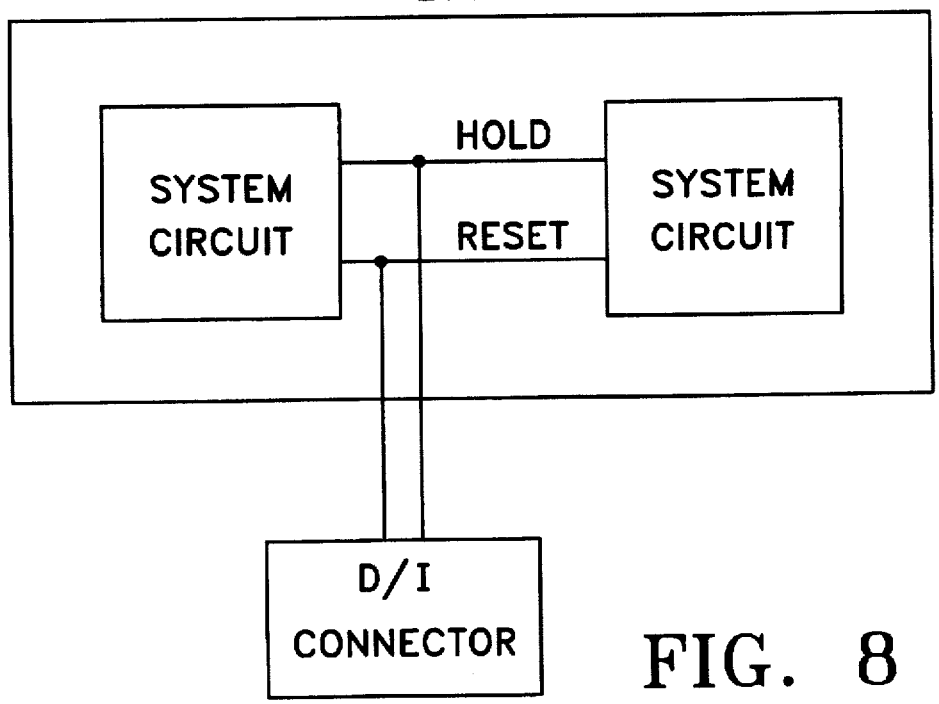
FIG. 8 illustrates a flow diagram for the programmable traction pull/hold phase control switch.

Referring to FIG. 4, a slant view of the adoptive traction modality with biofeedback (hereinafter referred to as "Traction Control System") of the invention is illustrated. The Traction Control System comprises five basic units namely, a main controller 1, a single channel high signal-to-noise ratio EMG scanner and processing units 2, a main controller/ EMG scanner interface (the interface not shown in FIG. 4), a traction force control interface 4 and a traction control window graphical display interface 5.

Figure 1:
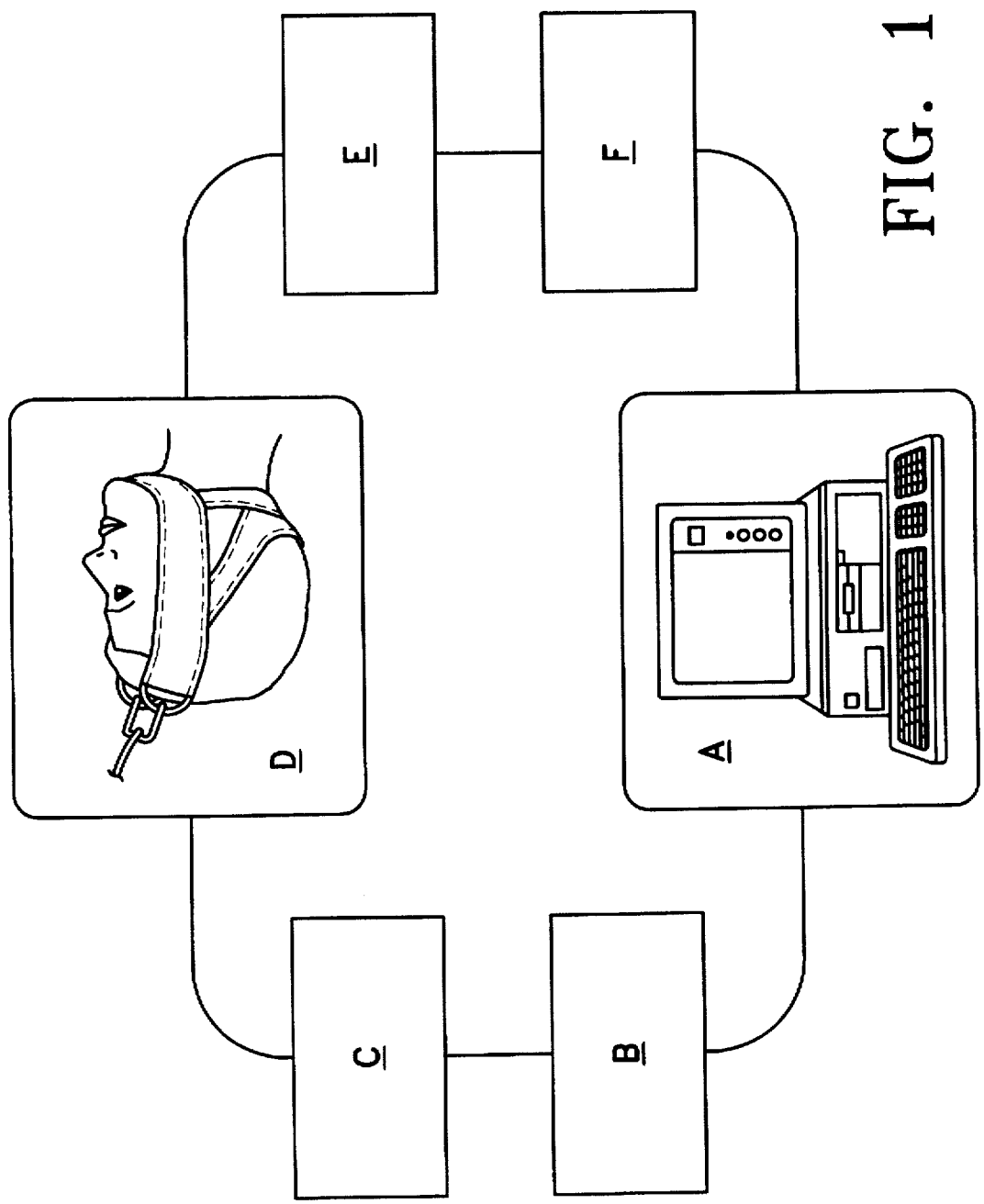
FIG. 1 depicts the hardware configuration of the EMG biofeedback controlled traction modality of the present invention.

Referring to FIG. 1, the hardware configuration of the Traction Control System is depicted in which the main controller A is connected with a main controller/traction actuator interface B from which the output from the main controller A passes to a traction actuator C which provides the power and the traction force adjusting mechanism for the traction machine D, from which the muscle activity is received by and recorded to the EMG scanner and signal processing unit E. After the EMG scanner and signal processing unit E completes its process of the received muscle activity, the EMG feedback signals are sent through an EMG scanner/main controller interface F to the main controller A to initiate another cycle of adaptive traction control therapy.

Figure 2:
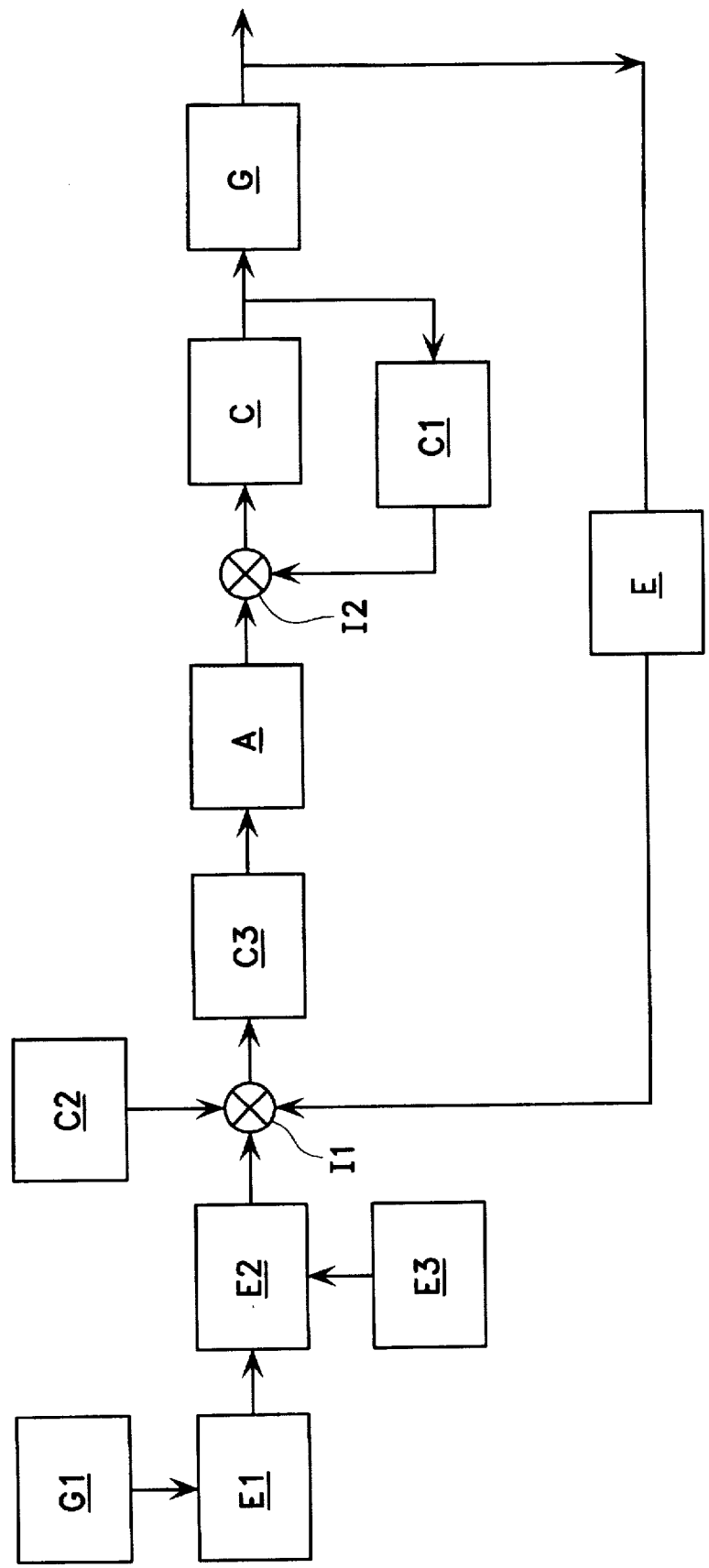
FIG. 2 is a block diagram illustrating the events of sequences for the closed loop EMG traction modality.

Referring to FIG. 2, the events of sequences for the closed loop EMG biofeedback traction control are shown. First of all, when a patient G is received for traction therapy, a therapist will enter by keyboard or touch screen the patient's information such as age, sex, skin fold etc. through a patient information entry mode G1 to the main controller A. Such information is then processed through an EMG upper and lower limit data base E1 to determine the adequate EMG upper and lower limits for said patient G., which are calculated by controller A automatically. Once the limits are set, the therapist can enter the desirable traction force control parameters through a traction pull phase initiator C2 and the desirable traction time control parameters through a traction remaining time controller C3 prior to the commencement of the traction by activating a traction actuator C through a traction force sensor C1. During traction, the surface EMG signal E3 of selected paraspinal muscle will be received and processed by an EMG scanner E from where the actual EMG signals will be biofeedbacked to the main controller A through a main controller/EMG scanner interface I1 to be continuously monitored and displayed in the control panel for the purpose of visual feedback and in-process therapeutic assessment. By comparing actual monitored EMG signal and calculated controlled EMG limits, an optimal traction force can be determined through control rules in main controller A. The control rules result in a deterministic logic expression, which use the on-line monitored surface EMG signal and a "controlled EMG constrains" for inputs. The output of the control rules is a safe traction force adjusting voltage.

Referring further to FIG. 4, the details of the Traction Control System are now described. The main controller 1 comprises a main computer 10 and a monitor 11. The monitor 11 is capable of performing certain graphical displays related to muscle activity or traction force control through a graphical display interface 50 compatible with the operation of Microsoft window programs. The main computer may be a personal computer or any other type of computer generally used in the field of engineering. The computer 10 may be further equipped with an analog/digital converter (A/D converter), a digital/analog converter (D/A converter), a sound card and an image input card. In order to implement a audiovisual system, a set of sound amplifiers 42 is connected to the sides of the main controller 1, with which a cassette player 40, a CD player 41 or any other multimedia audiovisual system may be connected. The traction force control and adjustment software is loaded inside the main computer 10.

Figure 3:
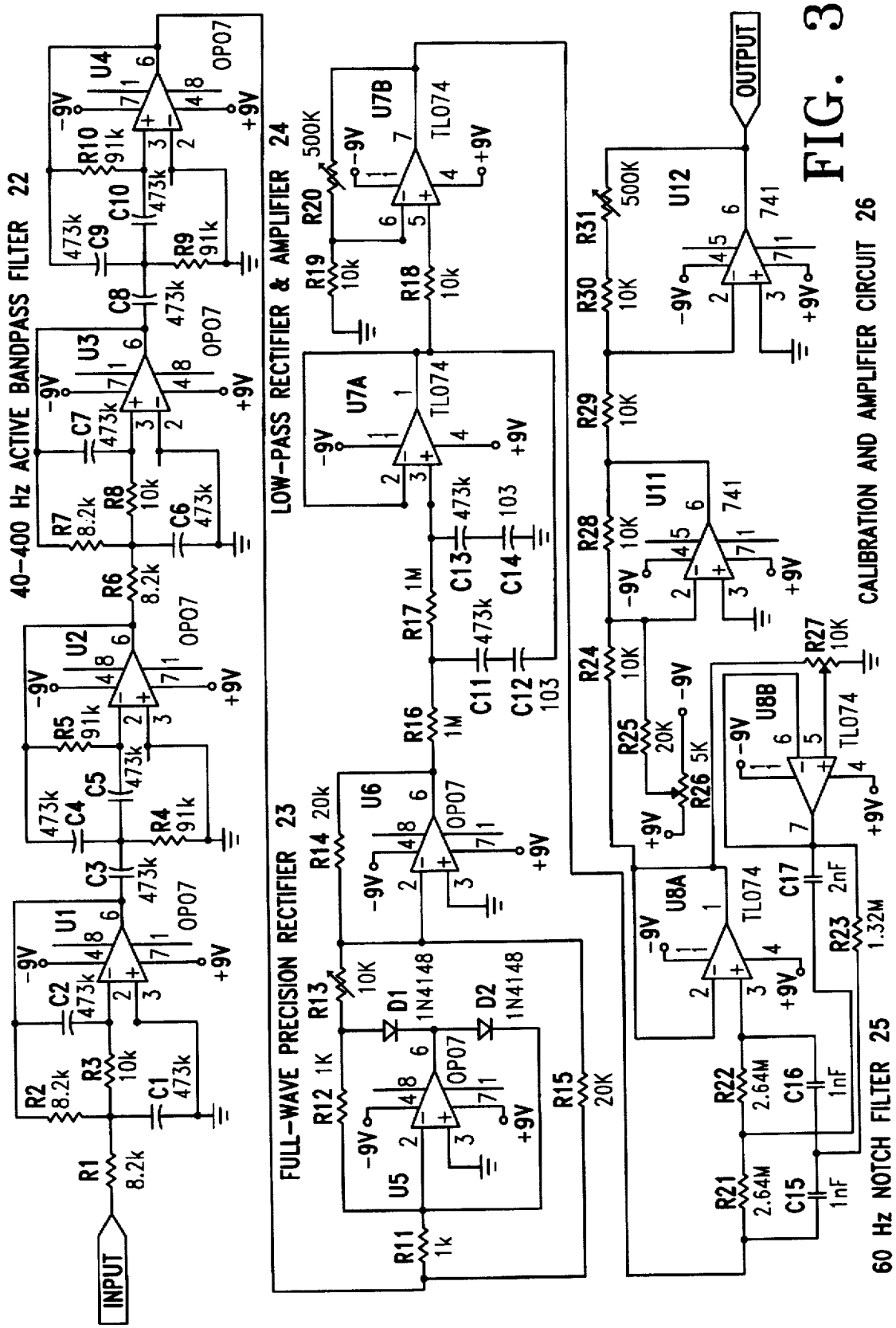
FIG. 3 shows the electrical circuit designs for the EMG scanner and processing units.

The single channel high signal-to-noise ratio EMG scanner system and signal processing units 2 comprises an EMG scanner 20 which includes a commercially available high input impedance surface electrode 21 and a signal processing and augmentation device (as shown in FIG. 4 as a part of EMG scanner 20). The signal processing and augmentation device consists of several subunits whose electrical circuits are shown in FIG. 3, including a 60 Hz notch filter 25, a fourth order Butterworth band pass filters 22, a precise full wave rectifier 23, a second order passive Butterworth low pass filter 24 and a calibration and amplifier circuit 26. Through this EMG scanner and signal processing unit 20, the muscle activity can be detected as an input and a linear enveloped EMG value can be generated as an output. The interface between the EMG scanner system and the main controller is a multi-functional DAS card through which the EMG scanner system and the main controller is connected and communicated. This DAS card features an 8 ms 12 bits A/D converter, a 12 bits double-buffered D/A converter and a 16 digital inputs and digital outputs to convert the messages received from and delivered between the two systems. The software drive of this DAS card includes dynamic link library (DLL) which enables the development of the control software with Microsoft Window 3.1 programs and Microsoft C++ tools. The sampling rate of proposed EMG control system is approximately 10 Hz.

The traction force control interface 4 is implemented and stored inside an analog signal control box 31 which is adjustably attached on a traction platform frame 30. The analog signal control box comprises a plurality of programmable electrical switches which are, individually and respectively, capable of controlling the power on/off, the traction force adjustments, the start/stop modes and the traction pull/hold interruption signals of the traction actuator as shown jointly in and from FIG. 5 to FIG. 9. These switches work in concert with a digital output (D/O) port and a digital input (D/I) port installed inside the main computer 10 to control the power, the traction force adjustments and the traction pull/hold phase of the traction actuator.

Figure 9:
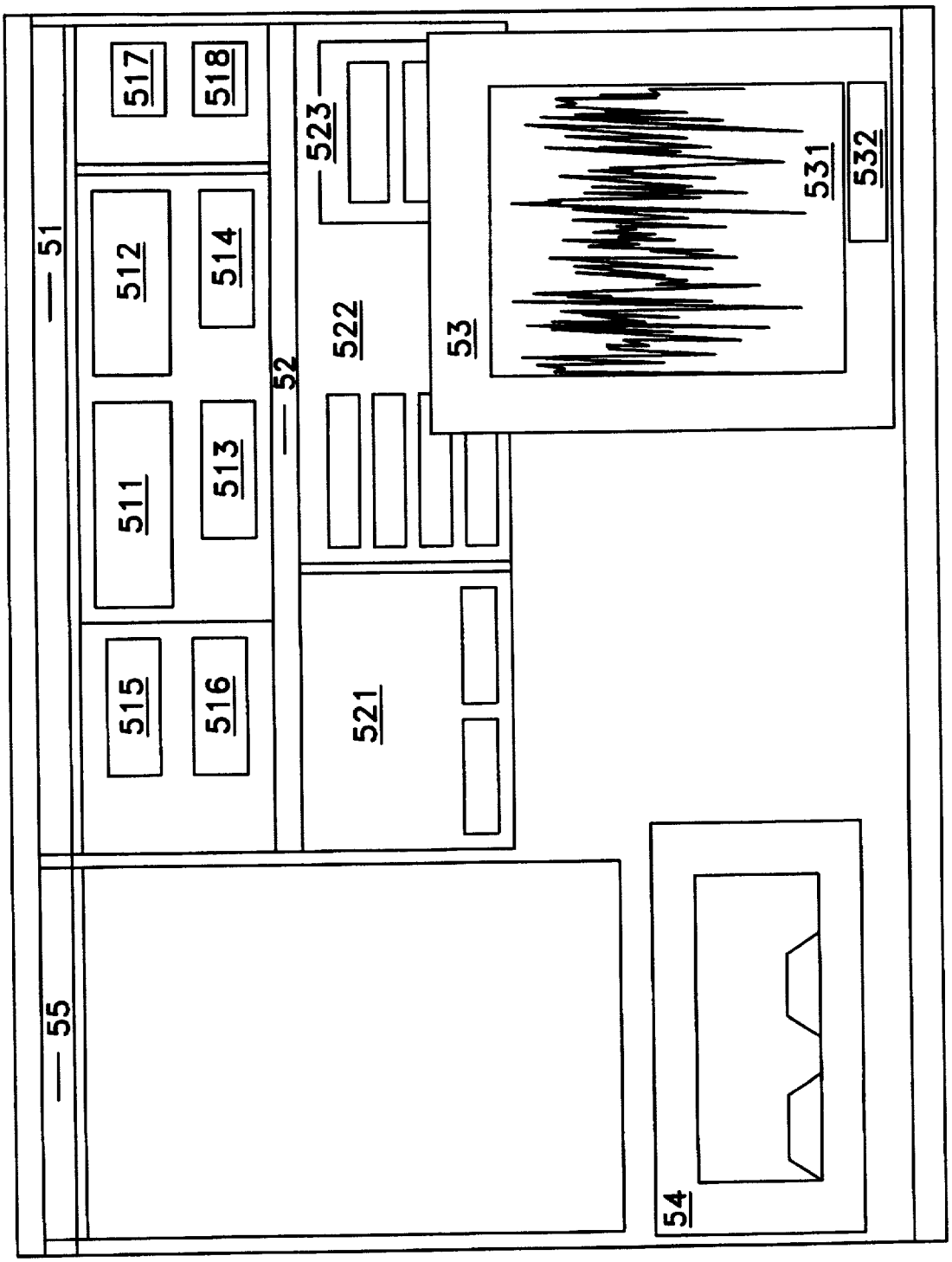
FIG. 9 illustrates the window based graphical display interface for traction control.

Referring now to FIG. 9, the traction control window graphical display interface 5 will be described. The traction control window graphical display interface 5 comprises a graphical display interface 50 compatible with the operation of Microsoft window programs or may be modified to be compatible with other operating systems if desirable. The graphical display interface 50 consists mainly of a traction control window 51, a status window 52, an EMG real-time signals or patterns window 53, a traction force patterns window 54 and a patient data window 55. The traction control window 51 performs digital displays for remaining traction time 511 and current traction weight 512. Various control buttons for traction power on/off 515, traction start/stop 516, traction force adjustment 514, traction time adjustment 513, traction pull phase control button 517 and traction hold phase control button 518 are also incorporated in the control panel which can be activated through keyboard and touch screen.

Still referring to FIG. 9, the status window 52 is capable of displaying a variety of messages includes a warning signal window 521, a status warning window 522 and a warning record window 523. The EMG signals or patterns window 53 is capable of performing graphical displays including real-time EMG signal patterns 531 and an EMG sensitivity adjustment button 532 to set up and adjust the resolution and detection limits for input signal display. The traction force window 54 displays the actual traction force produced by the traction actuator in traction pull and hold phases. The patient data window 55 displays a patient's information (i.e. name, medical record number, age, height, and weight) and prior system diagnostic data. In additional to visual displays, audio system was added to provided additional biofeedback and background music during traction.

The use of the Traction Control System according to the invention for treating a patient with intervertebral disc herniation and spondylosis is now described to illustrate the advantageous benefits provided by this invention as compared to other commercial open loop traction machines. When a new patient arrives, the attending therapist will enter the patient's information such as name, registration number, age, sex, skin fold, weight, height through the main computer 10 either by keyboard or by touch screen through the patient data window 55 on the monitor 11. The main computer 10 will prompt the monitor 11 to display all the entered information for the therapist's confirmation and automatically display the suggested traction force and pull/hold time and sequences which are considered to be most suitable and optimal for that patient calculated based on the patient's information against the stored data base. For an existing patient who has been receiving ongoing treatments, the computer will automatically display the patient's previous therapeutic information and treatment records such as prior traction force, number of times prior traction exceeding the upper or lower limits, any registered warning and the number of traction treatments.

The therapist may reconfirm the calculated optimal traction therapeutic protocols (i.e., traction force and pull/hold time sequence) through the traction control window 51 before treating the patient. Once the therapy commences, the therapist may constantly monitor and supervise the progress of treatment relating to remaining traction time and current traction force through screen locations for remaining traction time 511 and current traction force 512. The traction starts when a traction stripe 100 (shown in FIG. 4) is positioned at a patient's paraspinal region and a high input impedance surface electrode 21 is appropriately attached onto the patient's paraspinal region. During traction, the surface EMG signal of selected paraspinal muscle will be continuously monitored and displayed in the control panel for the purpose of visual feedback and in-process therapeutic assessment. The EMG signals detected from paraspinal muscle contraction is received by surface electrode 21 from which the signals is further treated and augmented to eliminate the 60 Hz signal noise by the 60 Hz notch filter 25, and to retain 40–400 Hz signals by the fourth order Butterworth band pass filters 22, the resulting signals are further processed through the precise full wave rectifier 23 and the second order passive Butterworth low pass filter 24 to produce a linear, enveloped loop signal which is processed once more by the 60 Hz notch filter 25 to eliminate and tare the undesirable background noises before the signals are finally augmented by the calibration and amplifier circuit 26 to generate a high signal-to-noise ration EMG signal.

The above processed EMG signals are subsequently sent to and received by the main computer 10 at which the signals are converted to digital signals by the A/D converter. The digital signals are compared with the upper and lower EMG controlled limits to determine the safety status of the ongoing traction therapy and to verify the degree of adequacy of the actual traction force. These two parameters are integrally incorporated into the traction actuator to make timely adjustments to the actual traction force and the remaining traction time as will be shown as digital displays at the windows designated for the remaining traction time 511 and the current traction force 512. If the detected paraspinal EMG signal exceeds the above stated control limits for three to five seconds, the traction force for next pulling period will be adaptively reduce for safety operation to avoid undesirable muscle convulsion or aggravated injury. In the meantime, the warning signal window 521 is activated to flash the warning signals and sound automatically. The therapist, once being informed of the warning status, may also manually adjust the traction force and remaining traction time by touching the windows locations designated for the remaining traction time 511 and the current traction force 512.

Figure 10:
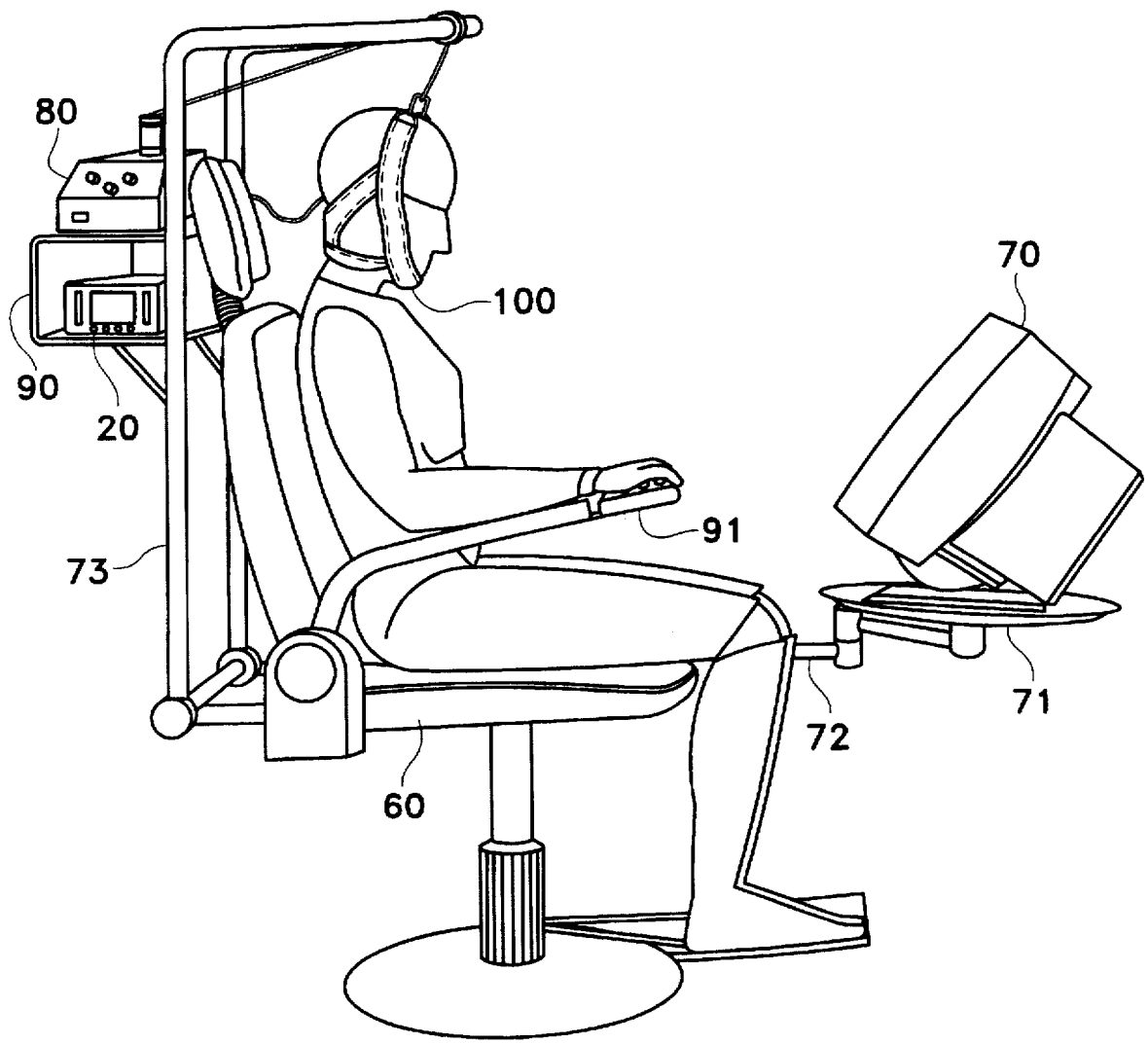
FIG. 10 shows the traction modality is modified to become a single operable unit.

Turning now to FIG. 10, the various parts of the Traction Control System including a traction platform frame 30 and other accessory equipments as shown in FIG. 4, can be integrated with a treatment chair 60 to form a single operable traction unit. In addition to the tractor platform frame 30 and the treatment chair 60, the integrated unit further comprises a main controller and a computer monitor 70, a supporting frame 71 for supporting the main controller and the computer monitor 70, a tractor control box 80, an EMG scanner and signal processing unit 20, a case 90 for accommodating the EMG scanner and signal processing unit 20, a traction stripe 100 and electronic control buttons 91. The main computer monitor 70 is fixedly installed on the supporting frame 71 which is rotatably mounted to a front extension frame 72 of the treatment chair 60. The tractor control box 80 and the EMG scanner and the signal processing unit 20 are fixedly installed on the case 90 which is perpendicularly fixed to a rear extension frame 73 of the treatment chair 60. The electronic control buttons 91 are fixedly installed on the front arm portion of the treatment chair 60 for controlling the main controller and the computer monitor 70, the backward or forward slidings of the chair 60, and the setting angles of the traction stripe 100. In addition, this design allows the patient to move the main computer monitor 70 directly in front of his sight to be well informed of the muscle relaxation status and the traction parameters described above. Moreover, this design will remind a patient to adjust his own posture from time to time during traction to practice self-relaxation to achieve an optimal therapeutic effects when the warning signals are flashing.

Figure 11:
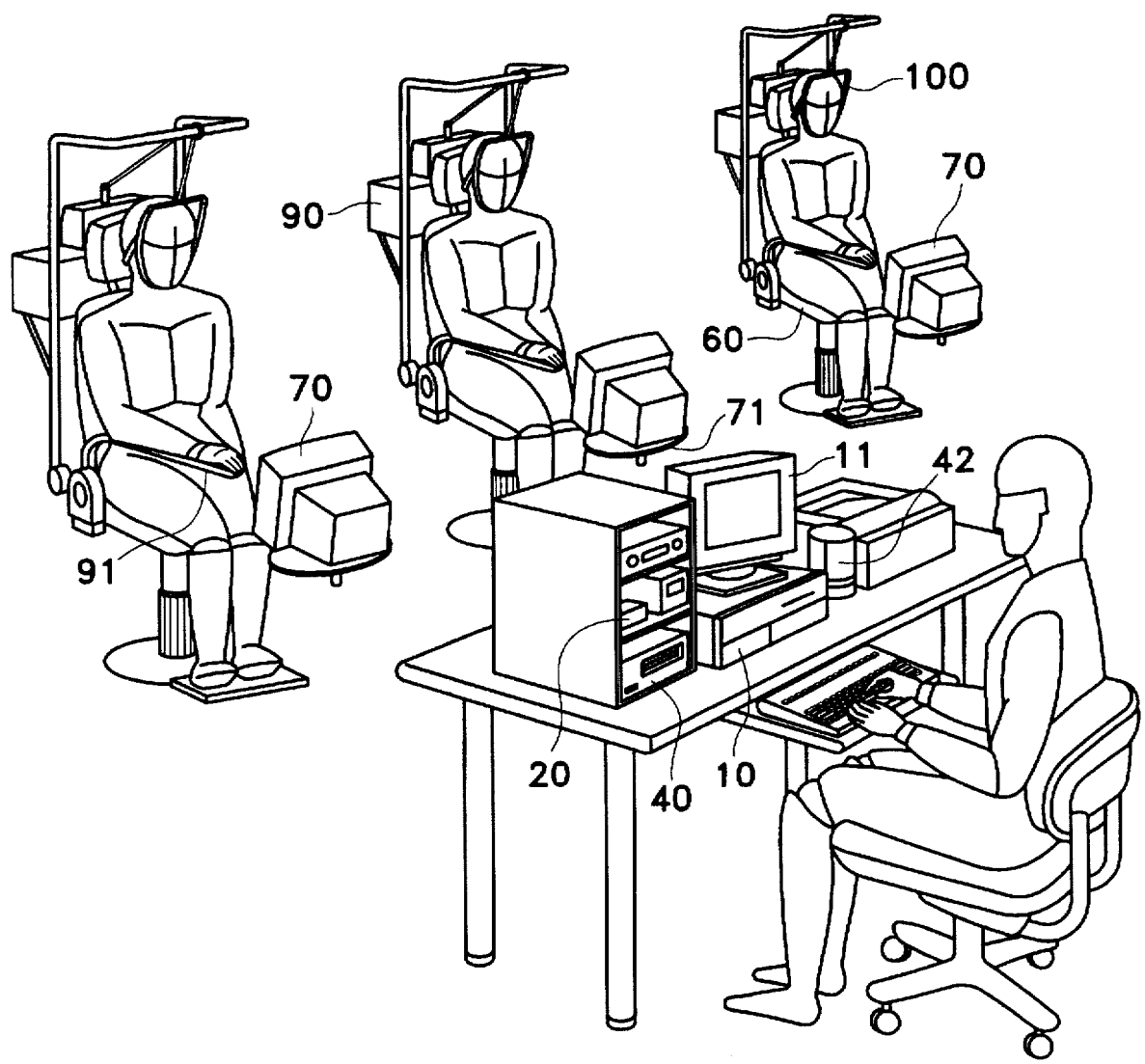
FIG. 11 shows a centralized traction control system consisting of a series of single operable traction units connected to a centralized main controller.

Referring to FIG. 11, the Traction Control System of the invention can be further integrated to establish a centralized traction control system in which a series of single operable traction units are connected to a control center so that one therapist can simultaneously monitor a number of patients. To achieve this purpose, the main computer 10 of each of the single operable traction units is networked with the main computer 10 located at the control center through a cable, optical fiber or wireless communication network to transmit the EMG signals and other traction parameters from each of the operation units to the control center. The therapist at a remote control center, by inquiring into the information displayed by the graphical display interface 50, can monitor and control the traction weight, the remaining time, the in-process status for each of the patients.

The Traction Control System disclosed by the invention can be integrated with multimedia audiovisual systems to create a biofeedback traction system. For instances, as shown in FIG. 4, the main computer 10 is integrated with the cassette player 40, the CD player 41, or any other commercially available multimedia accessories to produce a series of pleasant and scenic background pictures on the monitor 11 or to broadcast a series of soft and gentle music through the amplifier 42 during the traction therapy. It has been reported in psychiatric medicine that if a patient is provided with a pleasant and scenic environment coupled with soft and relaxing background music, a therapeutically active phenomena namely, "relaxation biofeedback", may take place inside the patient's physiological system which will stimulate the production of the so-called "Alpha" signals for the control of the patient's autonomous nervous system. According to the invention, when a patient's surface EMG signal exceeding the controlled limits, the main computer monitor 70 will automatically shift to the multimedia control mode to activate the audiovisual systems which will induce and initiate the "biofeedback" process to slow down the patient's muscle activity and to avoid undesirable injuries due to continuous muscle contractions during the traction. Thus, one unique feature of the invention is to provide for a novel Traction Control System capable of integrating with any entertainment or amusement device to enhance therapeutic effects through the mechanism of biofeedback.

Whereas the present invention has been descried with respect to a specific embodiment thereof, it will be understood that various changes and modifications will be suggested to one skilled in the art and it is intended to encompass such changes and modifications as fall within the scope of the appended claims.

We claim:

1. An adaptive traction modality with closed loop traction force control based on EMG biofeedback signals from a neuro-muscular lesion of a patient for rehabilitation, comprising:

a main controller for the control of traction force;

a single channel high signal-to-noise ratio EMG scanner and signal processing units for receiving and processing EMG signals from the neuro-muscular lesion into displayable data;

a main controller/EMG scanner interface to provide a communication means between said main controller and said EMG scanner and signal processing units for closed loop traction force monitor and adjustment;

a traction force control interface to provide a communication means between said main controller and said traction modality for traction force control; and a traction control window graphical display interface to display said data and to adjust traction force;

means for adaptively adjusting traction force based on EMG biofeedback signals includes entering the patient's information through said graphical display interface to said main controller to calculate a upper and lower EMG control limits, receiving said EMG biofeedback signals from said lesion and comparing the same with said control limits to determine an optimal traction force for adaptive traction force control.

2. An adaptive traction modality according to claim 1 wherein said single channel high signal-to-noise ratio EMG scanner and signal processing units comprise a 60 Hz notch filter, a fourth order Butterworth band pass filters, a precise full wave rectifier, a second order passive Butterworth low pass filter and a calibration and amplifier to reduce undesirable background noise and argument the EMG signals.

3. An adaptive traction modality according to claim 1 wherein said traction control window graphical display interface comprises a graphical display interface consisting mainly of a traction control window, a status window, an EMG signals or patterns window, a traction weight window and a patient data window for on-line monitor and adjustment of traction force.

4. An adaptive traction modality according to claim 3 wherein said traction control window further comprises digital display means for displaying remaining traction time and current traction force during the traction.

5. An adaptive traction modality according to claim 4 wherein said traction control window further comprises digital control means for traction power on/off, traction start/stop, traction force adjustment, traction time adjustment, traction pull phase control and traction hold phase control.

6. An adaptive traction modality according to claim 4 wherein said digital display means for displaying remaining traction time and current traction force is adjustable and based on on-line monitoring and processing of the actual EMG signals from the neuro-muscular lesion.

7. An adaptive traction modality according to claim 3 wherein said status window comprises a warning signal display window, a status warning window and a warning record window to display a variety of warning messages when the actual EMG signals recorded from the neuromuscular lesion exceeding a predetermined control limits resulting from improper traction control.

8. An adaptive traction modality according to claim 7 wherein said warning messages may be an visible digital display light, a red flashing light, a warning voice or any other audio sound effects.

9. An adaptive traction modality according to claim 3 wherein said EMG signals or patterns window comprises graphical display means for actual-time EMG signal patterns and an EMG sensitivity adjustment button to set up and adjust the detection limits for input signal display.

10. An adaptive traction modality according to claim 3 wherein said traction force window is capable of displaying a actual traction force produced by a traction actuator in traction pull and hold phases.

11. An adaptive traction modality according to claim 3 wherein said patient data window is capable of displaying a patient's information such as name, medical record number, age, height, weight and prior system diagnostic data.

12. An adaptive traction modality according to claim 1 wherein said traction force control interface comprises an analog signal control box adjustably attached on a traction platform frame wherein said analog signal control box comprises a plurality of programmable electrical switches which are, individually and respectively, capable of controlling the power on/off, the traction force adjustments, the start/stop modes and the traction pull/hold interruption signals of a traction actuator.

13. An adaptive traction modality according to claim 1 wherein said traction modality is physically integrated with a treatment chair to form a single operable traction unit comprising a main computer monitor fixedly installed on a supporting frame which is rotatably mounted to a front extension frame of the treatment chair, a case which is perpendicularly fixed to a rear extension frame of the treatment chair for the mounting of a tractor control box and an EMG scanner and electronic control buttons fixedly installed on the front arm portion of the treatment chair for conveniently controlling the movement of the main computer monitor and the backward or forward sidings of the chair.

14. An adaptive traction modality according to claim 13 wherein a series of said single operable traction units are further connected to and networked together with a main controller to form a centralized traction control system.

15. An adaptive traction modality according to claim 1 further comprises a multimedia audiovisual system to produce a series of pleasant and scenic background pictures on a monitor or to broadcast a series of soft and gentle music through an amplifier during the traction therapy to create a biofeedback traction system to ease a patient's overly excited muscle activity and to enhance therapeutic effects.

* * * * *